US010934251B2

(12) United States Patent
Parthasaradhi Reddy et al.

(10) Patent No.: US 10,934,251 B2
(45) Date of Patent: *Mar. 2, 2021

(54) PROCESS FOR THE PREPARATION OF LOMITAPIDE

(71) Applicant: Hetero Research Foundation, Hyderabad (IN)

(72) Inventors: Bandi Parthasaradhi Reddy, Telangana (IN); Kura Rathnakar Reddy, Telangana (IN); Bandi Vamsi Krishna, Hyderabad (IN); Jambula Mukunda Reddy, Telangana (IN)

(73) Assignee: HETERO RESEARCH FOUNDATION, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/797,498

(22) Filed: Feb. 21, 2020

(65) Prior Publication Data
US 2020/0190018 A1  Jun. 18, 2020

Related U.S. Application Data

(60) Continuation of application No. 16/008,360, filed on Jun. 14, 2018, now abandoned, which is a division of application No. 15/524,391, filed as application No. PCT/IB2015/058521 on Nov. 4, 2015, now Pat. No. 10,023,526.

(30) Foreign Application Priority Data

Nov. 5, 2014 (IN) .......................... 5536/CHE/2014

(51) Int. Cl.
*C07C 231/02* (2006.01)
*C07D 211/58* (2006.01)
*C07C 231/12* (2006.01)
*C07C 67/293* (2006.01)
*C07C 69/157* (2006.01)
*C07C 51/367* (2006.01)
*C07C 62/32* (2006.01)

(52) U.S. Cl.
CPC .......... *C07C 231/02* (2013.01); *C07C 51/367* (2013.01); *C07C 62/32* (2013.01); *C07C 67/293* (2013.01); *C07C 69/157* (2013.01); *C07C 231/12* (2013.01); *C07D 211/58* (2013.01); *C07C 2603/18* (2017.05)

(58) Field of Classification Search
None
See application file for complete search history.

(56) References Cited

U.S. PATENT DOCUMENTS

| 5,712,279 | A | 1/1998 | Biller |
| 5,760,246 | A | 6/1998 | Biller |
| 5,885,983 | A | 3/1999 | Biller |
| 6,472,414 | B1 | 10/2002 | Biller |
| 10,023,526 | B2 * | 7/2018 | Parthasaradhi Reddy .................. C07C 231/02 |
| 2018/0291773 | A1 | 10/2018 | Bandi et al. |

FOREIGN PATENT DOCUMENTS

| WO | 9626205 | 8/1996 |
| WO | 9743257 A1 | 11/1997 |
| WO | 9964037 | 12/1999 |

OTHER PUBLICATIONS

International Preliminary Report on Patentability: PCT/IB2015/058521; Filed Nov. 5, 2014; dated May 9, 2017.
International Search Report; International Application No. PCT/IB2015/058521; International Filing Date Nov. 5, 2014; dated Apr. 18, 2016 (6 pages).

* cited by examiner

*Primary Examiner* — Amy C Bonaparte
(74) *Attorney, Agent, or Firm* — Cantor Colburn LLP

(57) ABSTRACT

The present invention relates to a process for preparing Lomitapide or its pharmaceutically acceptable salt thereof having high purity with acceptable levels of impurities.

13 Claims, No Drawings

PROCESS FOR THE PREPARATION OF LOMITAPIDE

CROSS-REFERENCE TO RELATED APPLICATIONS

This application is a continuation of U.S. application Ser. No. 16/008,360 filed on Jun. 14, 2018, which is a divisional of U.S. Ser. No. 15/524,391, filed on May 4, 2017, Issued as U.S. patent Ser. No. 10/023,526, on Jul. 17, 2018, which is a § 371 of PCT/IB2015/058521, filed on Nov. 4, 2015, which claims priority to Indian Application 5536/CHE/2014 filed on Nov. 5, 2014, which is incorporated herein by reference in its entirety.

FIELD OF THE INVENTION

The present invention relates to a process for preparing Lomitapide or its pharmaceutically acceptable salt thereof having high purity with acceptable levels of impurities.

BACKGROUND OF THE INVENTION

Lomitapide chemically known as N-(2,2,2-trifluoroethyl)-9-[4-[4-[[[4'(trifluoromethyl)[1,1'-biphenyl]-2-yl]carbonyl]amino]-1-piperidinyl]butyl]-9H-fluorene-9-carboxamide having the following structure designated as Formula 1.

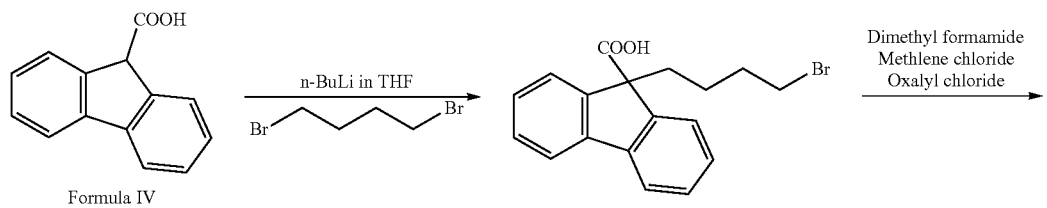

Lomitapide

Lomitapide is marketed as its mesylate salt under the trade name Juxtapid® as capsule; oral having dosage strengths Eq 5 MG Base, Eq 10 MG Base and EQ 20 MG Base, which inhibits the microsomal triglyceride transfer protein (MTP or MTTP) which is necessary for very low-density lipoprotein (VLDL) assembly and secretion in the liver.

Lomitapide and its pharmaceutically acceptable salts were disclosed in U.S. Pat. No. 5,712,279 A. This patent also discloses the preparation of Lomitapide by two different methods, which are shown below:

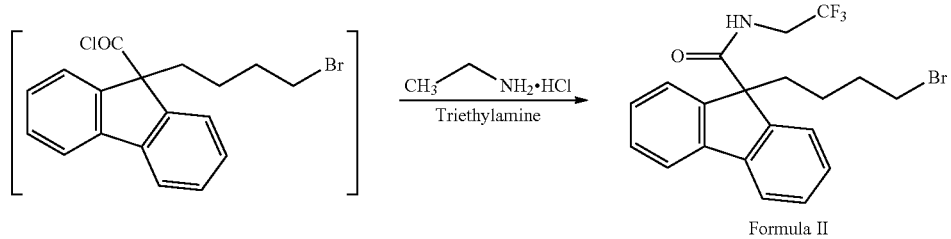

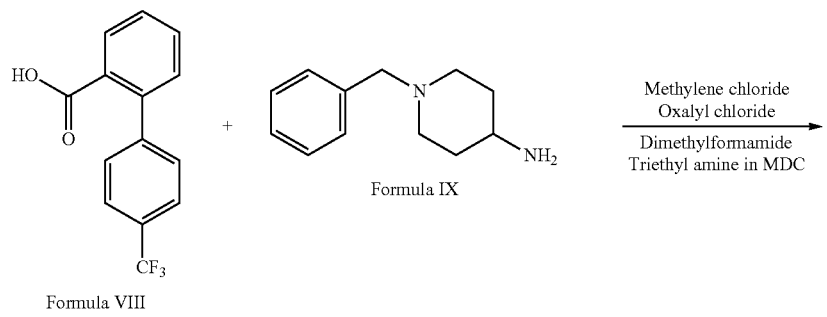

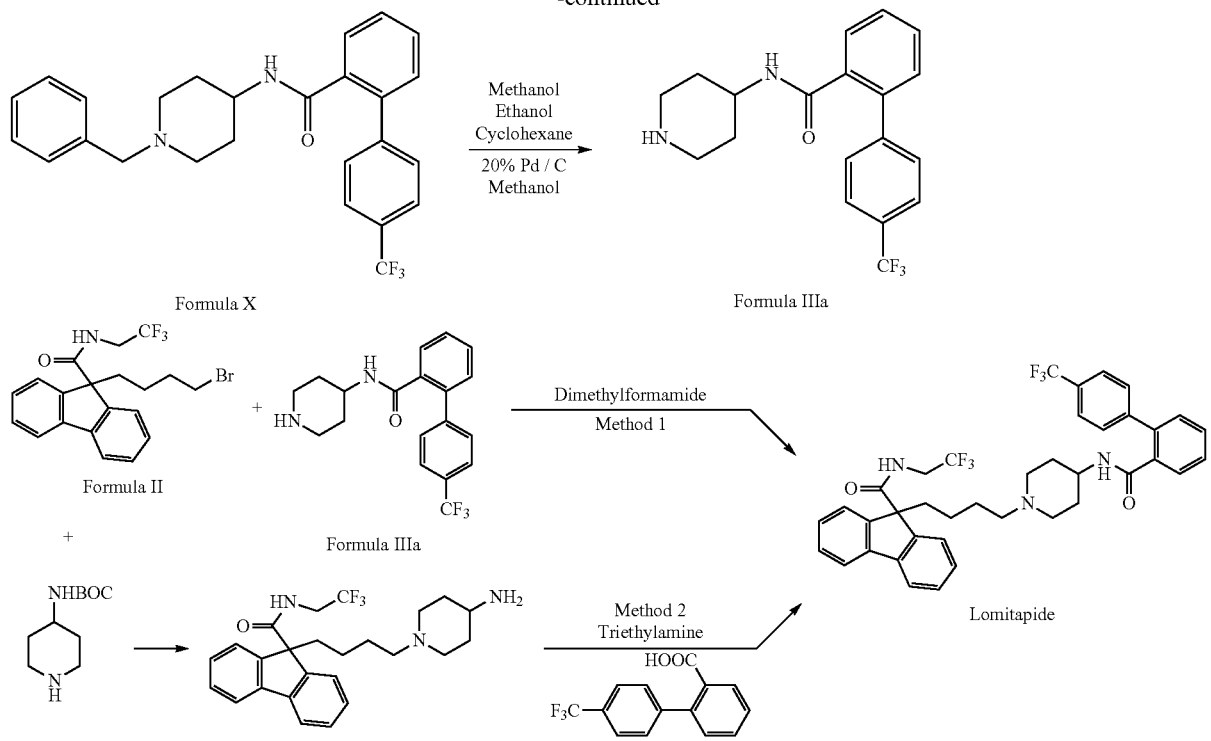

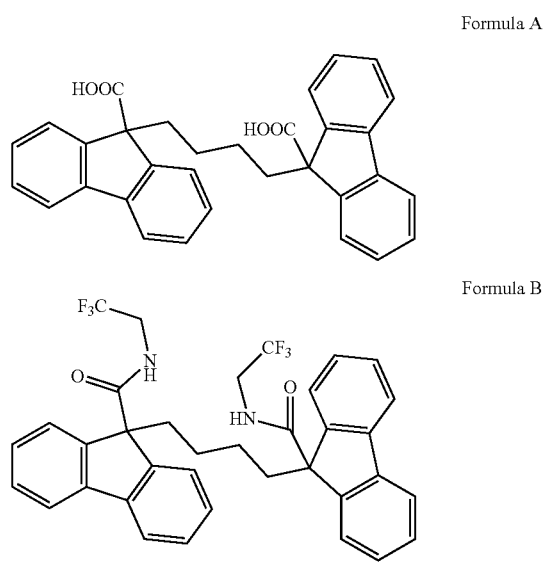

The process for the preparation of 9-(4-Bromobutyl)-N-(2,2,2-trifluoroethyl)-9H-fluorene-9-carboxamide of Formula II, comprises reacting 9-Fluorene carboxylic acid of Formula IV with 1,4-Dibromobutane in presence of n-BuLi in tetrahydrofuran, then chlorination with oxalyl chloride to form acid chloride compound as a crude oil, followed by amidation with 2,2,2-trifluoroethylamine hydrochloride in presence of triethylamine to yield 9-(4-Bromobutyl)-N-(2,2,2-trifluoroethyl)-9H-fluorene-9-carboxamide of Formula II.

The process for the preparation of piperidinyl biphenyl carboxamide derivative of Formula IIIa, comprises by reacting 4'-(trifluoromethyl)-2-biphenyl carboxylic acid of Formula VIII with oxalyl chloride in methylene chloride and dimethyl formamide, thereafter condensed with 4-amino-1-benzylpiperidine of Formula IX in presence of triethylamine in methylene chloride to yield N-(1-benzylpiperidin-4-yl)-4'-(trifluoromethyl)-[1,1'-biphenyl]-2-carboxamide of Formula X, which is deprotected using palladium/carbon in methanol and cyclohexane.

Lomitapide has been prepared by condensing bromobutyl 9H-fluorene carboxamide derivative of Formula II with piperidinyl biphenyl carboxamide derivative of formula IIIa in dimethylformamide or by condensing bromobutyl 9H-fluorene carboxamide derivative of Formula II with 4-tert-Boc-amino piperidine to give 9-(4-(4-aminopiperidin-yl)butyl)-N-(2,2,2-trifluoroethyl)-9H-fluorene-9-carboxamide and thereafter condensed with 4'-(trifluoromethyl)-2-biphenyl carboxylic acid in the presence of triethylamine.

Lomitapide hydrochloride salt has been prepared by purifying Lomitapide free base by Column Chromatography (SiO$_2$, MeOH:MeCl$_2$) and thereafter reacting with etheral HCl in Methanol.

The present inventors have found that the prior-art process is not suitable commercially or on industrial scale as the process yields Lomitapide having dimer impurities, shown below designated as Formula A and Formula B.

Further the process involves purification using column chromatography, which is not suitable in the commercial scale production.

Further, the process shown for the intermediate preparation yields the intermediate compound having less purity and low yields, as the reaction doesn't go complete.

Further, the present inventors has also observed that the Lomitapide prepared by the prior-art process yields Lomitapide having the purity of ≤85% (by HPLC), which needs further purifications and hence the process is not suitable economically.

U.S. Pat. No. 5,760,246 A discloses the synthesis of 9-(4-bromobutyl)-N-(2,2,2-trifluoroethyl)-9H-fluorene-9-carboxamide of Formula II, which is a shown below:

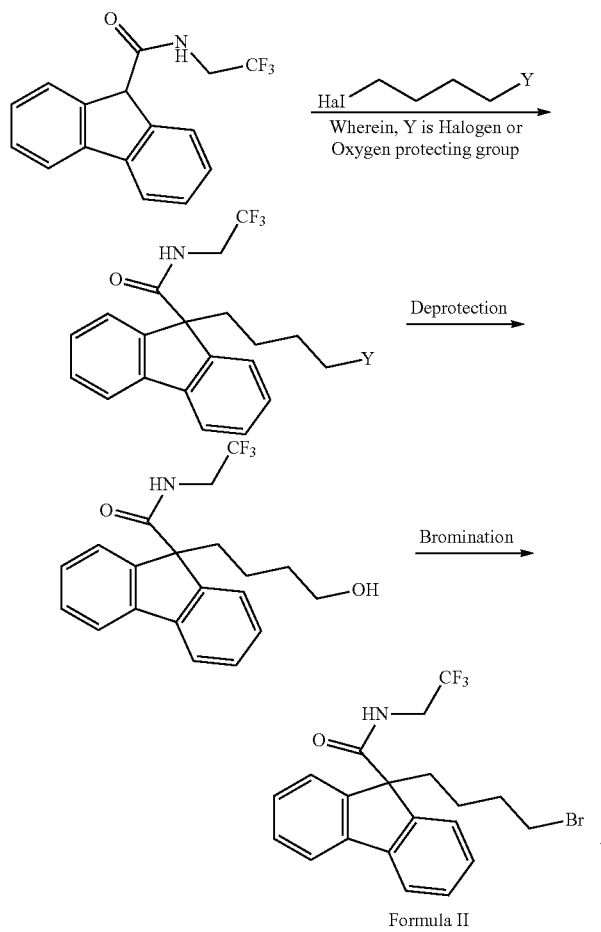

Alkylation of N-(2,2,2-trifluoroethyl)-9H-fluorene-9-carboxamide has been carried out by protecting alkane in presence of a base, wherein protecting group is selected from the group consisting of t-Bu(CH$_3$)$_2$Si or t-Bu(Ph)$_2$Si, followed by deprotection and bromination. The present inventors have repeated the process and found that the obtained intermediate compound has less purity, low yields, commercially not feasible and economically not cost effective.

In view of the above, there is a need for the improved, cost-effective, industrially applicable process for the preparation of Lomitapide or its pharmaceutically acceptable salt thereof as well as its intermediates having high yield, purity as well as acceptable levels of impurities.

Objectives

One objective of the present invention is to provide a process for the preparation of Lomitapide or its pharmaceutically acceptable salt thereof, which is industrially applicable, having high yield and purity with the acceptable levels of impurities.

Another objective of the present invention is to provide a process for the preparation of Lomitapide or its pharmaceutically acceptable salt thereof, which is cost effective and suitable economically.

Another objective of the present invention also provides intermediate compounds, which are useful in the preparation of Lomitapide or its pharmaceutically acceptable salt thereof.

SUMMARY OF THE INVENTION

The present invention provides a process for the preparation of Lomitapide or its pharmaceutically acceptable salt thereof, Formula I

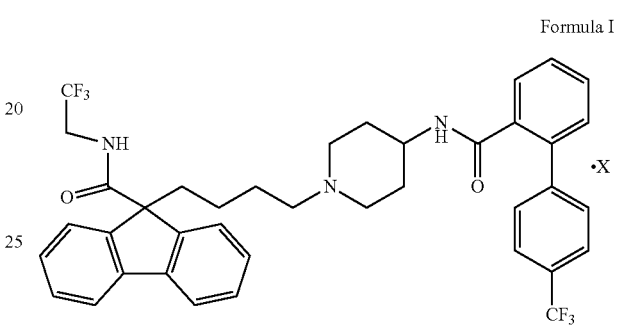

wherein X represents an acid salt,
which comprises,
i) condensing bromobutyl 9H-fluorene carboxamide derivative of Formula II Formula II

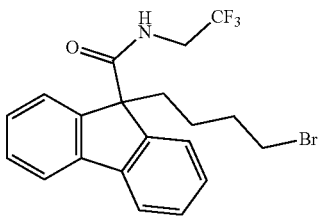

with salt of piperidinyl biphenyl carboxamide derivative of Formula III

Formula III

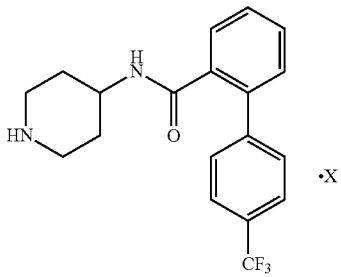

wherein X represents an acid salt
to yield Lomitapide freebase;
ii) optionally purifying Lomitapide freebase;
iii) optionally converting Lomitapide Free base to its pharmaceutically acceptable salt thereof; and iv) optionally purifying Lomitapide pharmaceutically acceptable salt thereof.

In another embodiment of the present invention provides a process for the preparation of bromobutyl 9H-fluorene carboxamide derivative of Formula II,

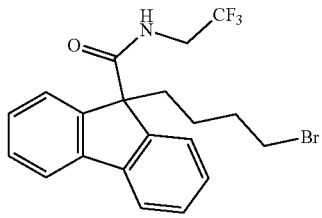

Formula II which comprises:

i) condensing 9H-fluorene-9-carboxylic acid of Formula IV

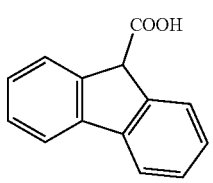

Formula IV with 4-bromobutyl acetate to yield 9-(4-acetoxybutyl-9H-fluorene-9-carboxylic acid of Formula V;

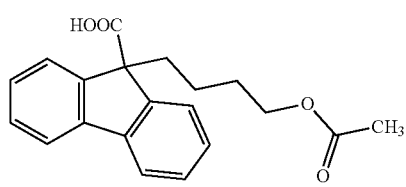

Formula V ii) optionally isolating the compound of Formula V;

iii) reacting the compound of Formula V with alkali hydroxide solution to yield 9-(4-hydroxybutyl)-9H-fluorene-9-carboxylic acid of Formula VI;

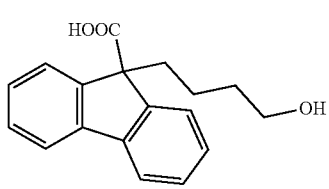

Formula VI iv) reacting the compound of formula VI with 2,2,2-trifluoroethane-1-amine hydrochloride salt to yield 9-(4-hydroxybutyl)-N-(2,2,2-trifluoroethyl)-9H-fluorene-carboxylic acid of Formula VII;

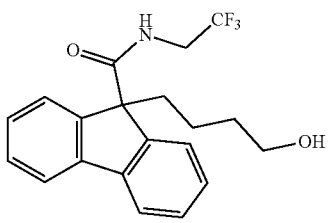

Formula VII v) reacting the compound of formula VII with bromine to yield bromobutyl 9H-fluorene carboxamide derivative of Formula II; and vi) optionally purifying the compound of Formula II.

In another embodiment of the present invention provides a process for the preparation of salt of piperidinyl biphenyl carboxamide derivative of formula III,

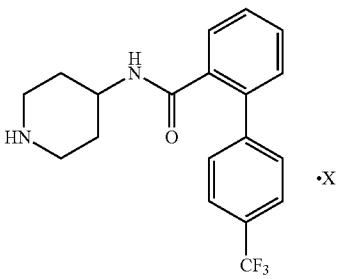

Formula III wherein X represents an acid salt.

which comprises:

i) condensing 4'-(trifluoromethyl)-[1,1'-biphenyl]-2-carboxylic acid of Formula VIII

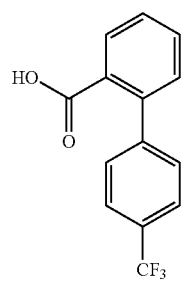

Formula VIII with 4-amino-1-benzyl piperidine of Formula IX

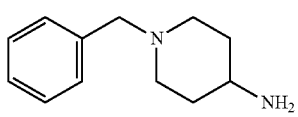

Formula IX to yield benzylpiperidine biphenyl carboxamide derivative of Formula X;

Formula X

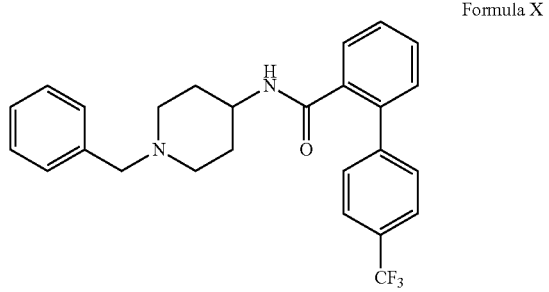 [SMILES: O=C(NC1CCN(Cc2ccccc2)CC1)c1ccccc1-c1ccc(C(F)(F)F)cc1]

ii) optionally isolating the compound of Formula X;
iii) optionally purifying the compound of Formula X;
iv) converting the compound of Formula X to the acid salt of piperidinyl biphenyl carboxamide derivative of formula III.

In another embodiment of the present invention provides intermediate compound, 9-(4-acetoxybutyl-9H-fluorene-9-carboxylic acid of Formula V Formula V

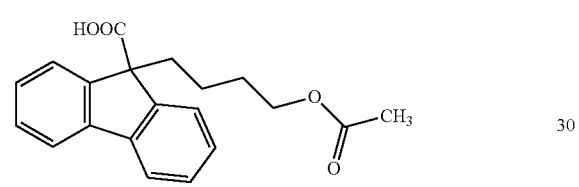

which is useful in the preparation of Lomitapide or its pharmaceutically acceptable salt thereof.

In another embodiment of the present invention provides intermediate compound, 9-(4-hydroxybutyl)-9H-fluorene-9-carboxylic acid of Formula VI Formula VI

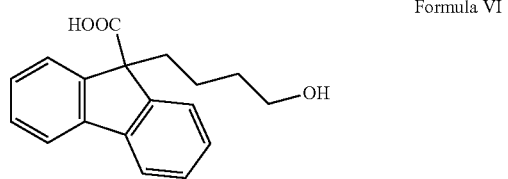 [SMILES: O=C(O)C1(CCCCO)c2ccccc2-c2ccccc21]

which is useful in the preparation of Lomitapide or its pharmaceutically acceptable salt thereof.

DETAILED DESCRIPTION OF THE INVENTION

The present invention relates to a process for the preparation of Lomitapide or its pharmaceutically acceptable salt thereof with acceptable levels of impurities, which comprises: reacting the bromobutyl 9H-fluorene carboxamide derivative of Formula II with salt of piperidinyl biphenyl carboxamide of Formula III in a solvent selected from the group comprising of alcohols, halogenated hydrocarbons, polar aprotic solvents, non-polar solvents, wherein alcohols are selected from the group comprising of aliphatic alcohols or aromatic alcohols, halogenated hydrocarbons are selected from the group comprising of chlorinated hydrocarbons, polar aprotic solvents are selected from the group compris-ing of organic nitriles, amides, ketones, ethereal solvents, esters in presence of a base selected from the group comprising of alkyl amines or organo or inorgano metallic reagents, metal hydrides, metal hydroxides or metal alkoxides to give Lomitapide Free base and optionally purifying Lomitapide Free base. Optionally converting Lomitapide free base to its pharmaceutically acceptable salt thereof by reacting Lomitapide Free base with an acid in a solvent selected from the group comprising of alcohols, halogenated hydrocarbons, polar aprotic solvents, non-polar solvents to yield Lomitapide pharmaceutically acceptable salt thereof and optionally purifying Lomitapide pharmaceutically acceptable salt thereof.

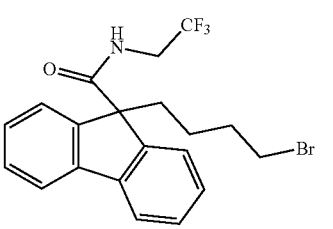

Formula II

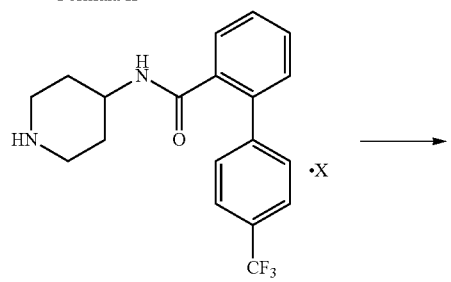

Formula III

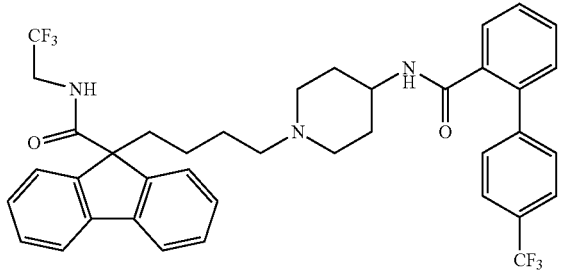

Lomitapide

|Acid

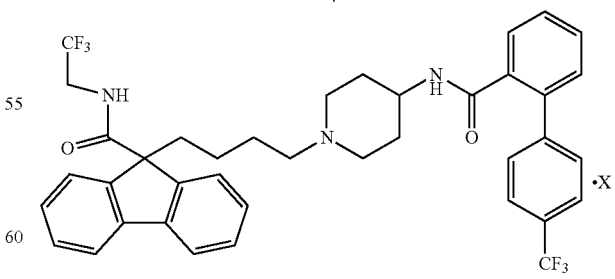

Formula I wherein X represents an acid salt.

In another embodiment of the present invention, aliphatic alcohols are selected from the group comprising of methanol, ethanol, n-propanol, isopropanol, n-butanol, pentanol, isobutanol, tertiary butanol, cyclopropanol, cyclobutanol, cyclopentanol, cyclohexanol or mixtures thereof, aromatic alcohols are selected form the group comprising of phenols, benzylalcohol or mixtures thereof; chlorinated hydrocarbons are selected from the group comprising of chloroform, ethylene chloride, methylene dichloride or mixtures thereof; organic nitriles are selected from the group comprising of aliphatic nitriles such as $C_2$-$C_8$ nitrile; Ketones are selected pound of Formula V thereafter reacting with alkali hydroxide solution in a solvent to yield 9-(4-hydroxybutyl)-9H-fluorene-9-carboxylic acid of Formula VI. Reacting the compound of formula VI with 2,2,2-trifluoroethane-1-amine hydrochloride salt in a solvent to yield 9-(4-hydroxybutyl)-N-(2,2,2-trifluoroethyl)-9H-fluorene-carboxylic acid of Formula VII and is reacting with bromine in a solvent to yield bromobutyl 9H-fluorene carboxamide derivative of Formula II and optionally purifying the compound of Formula II.

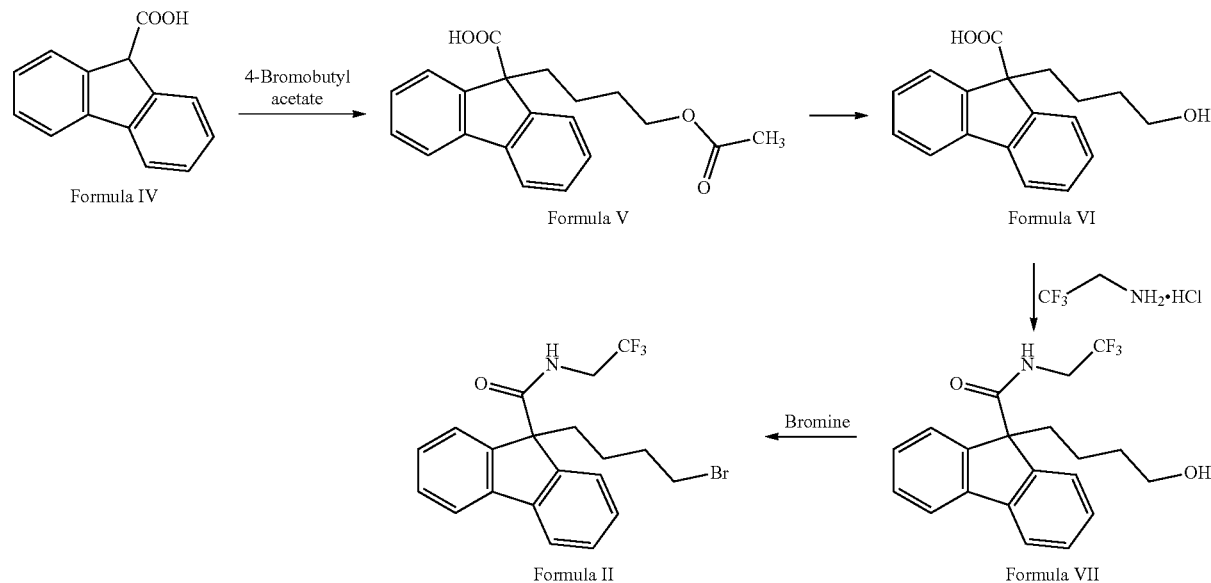

from the group comprising of aliphatic ketones such as acetone, dimethyl formamide, methyl ethyl ketone, methyl isobutyl ketone, cyclobutanone, cyclopentanone, cyclohexanone or mixtures thereof; esters are selected from the group comprising of methyl acetate, ethyl acetate, isopropyl acetate, isopropyl acetate or mixtures thereof; non-polar solvents are selected from the group comprising of butane, pentane, hexane, heptane, toluene, n-hexane, n-heptane; and ethereal solvents are selected from the group comprising of dimethyl ether, diethyl ether, diisopropyl ether, tetrahydrofuran, 1,4-dioxane and the like.

In another embodiment throughout the invention, the mixture of solvents means two or more solvents.

In another embodiment of the present invention, obtained Lomitapide or its pharmaceutically acceptable salt can be optionally purified by conventional methods.

The present invention also relates to a process for the preparation of bromobutyl 9H-fluorene carboxamide derivative of Formula II, which comprises: condensing 9H-fluorene-9-carboxylic acid of Formula IV with 4-bromobutyl acetate in a solvent selected from alcohols, halogenated hydrocarbons, polar aprotic solvents, non-polar solvents, wherein alcohols are selected from the group comprising of aliphatic alcohols or aromatic alcohols, halogenated hydrocarbons are selected from the group comprising of chlorinated hydrocarbons, polar aprotic solvents are selected from the group comprising of organic nitriles, amides, ketones, ethereal solvents, esters in presence of a base selected from the group comprising of alkyl amines or organo or inorgano metallic reagents, metal hydrides, metal hydroxides or metal alkoxides to yield 9-(4-acetoxybutyl-9H-fluorene-9-carboxylic acid of Formula V and optionally isolating the compound of Formula V thereafter reacting with alkali hydroxide solution in a solvent to yield 9-(4-hydroxybutyl)-9H-fluorene-9-carboxylic acid of Formula VI. Reacting the In another embodiment of the present invention, aliphatic alcohols are selected from the group comprising of methanol, ethanol, n-propanol, isopropanol, n-butanol, pentanol, isobutanol, tertiary butanol, cyclopropanol, cyclobutanol, cyclopentanol, cyclohexanol or mixtures thereof, aromatic alcohols are selected form the group comprising of phenols, benzylalcohol or mixtures thereof; chlorinated hydrocarbons are selected from the group comprising of chloroform, ethylene chloride, methylene dichloride or mixtures thereof; organic nitriles are selected from the group comprising of aliphatic nitriles such as $C_2$-$C_8$ nitrile; Ketones are selected from the group comprising of aliphatic ketones such as acetone, dimethyl formamide, methyl ethyl ketone, methyl isobutyl ketone, cyclobutanone, cyclopentanone, cyclohexanone or mixtures thereof; esters are selected from the group comprising of methyl acetate, ethyl acetate, isopropyl acetate, isopropyl acetate or mixtures thereof; non-polar solvents are selected from the group comprising of butane, pentane, hexane, heptane, toluene, n-hexane, n-heptane and ethereal solvents are selected from the group comprising of dimethyl ether, diethyl ether, diisopropyl ether, tetrahydrofuran, 1,4-dioxane and the like.

In another embodiment of the present invention, alkali hydroxides used throughout the invention are selected form the group comprising of sodium hydroxide, potassium hydroxide and the like.

The present invention also relates to a process for the preparation of piperidinyl biphenyl carboxamide derivative or acid salt thereof of Formula III, which comprises: condensing 4'-(trifluoromethyl)-2-biphenyl carboxylic acid of Formula VIII with 4-amino-1-benzylpiperidine of Formula IX in a solvent is selected from alcohols, halogenated hydrocarbons, polar aprotic solvents, non-polar solvents, wherein alcohols are selected from the group comprising of aliphatic alcohols or aromatic alcohols, halogenated hydrocarbons are selected from the group comprising of chlorinated hydrocarbons, polar aprotic solvents are selected from the group comprising of organic nitriles, amides, ketones, ethereal solvents or esters to yield N-(1-benzylpiperidin-4-yl)-4'-(trifluoromethyl)-[1,1'-biphenyl]-2-carboxamide of Formula X and optionally isolating and purifying the compound of Formula X. The obtained compound of Formula X is debenzylated using a metal catalyst to give the compound of Formula IIIa and is reacted with an acid selected from organic or inorganic acids to yield the compound of formula III.

ethereal solvents are selected from the group comprising of dimethyl ether, diethyl ether, diisopropyl ether, tetrahydrofuran, 1,4-dioxane and the like.

In another embodiment of the present invention, alkyl amines used throughout the invention are selected form the group comprising of diethylamine, triethylamine and the like; organo or inorgano metallic reagents used throughout the invention are selected form the group comprising of n-butyl lithium, sec-butyl lithium, t-butyl lithium and the like; metal hydrides used throughout the invention are selected form the group comprising of sodium hydride, potassium hydride and lithium hydride and the like; metal hydroxides used throughout the invention are selected form the group comprising of sodium hydroxide, potassium

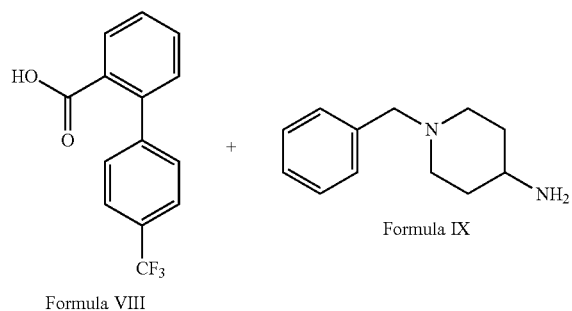

Formula VIII + Formula IX

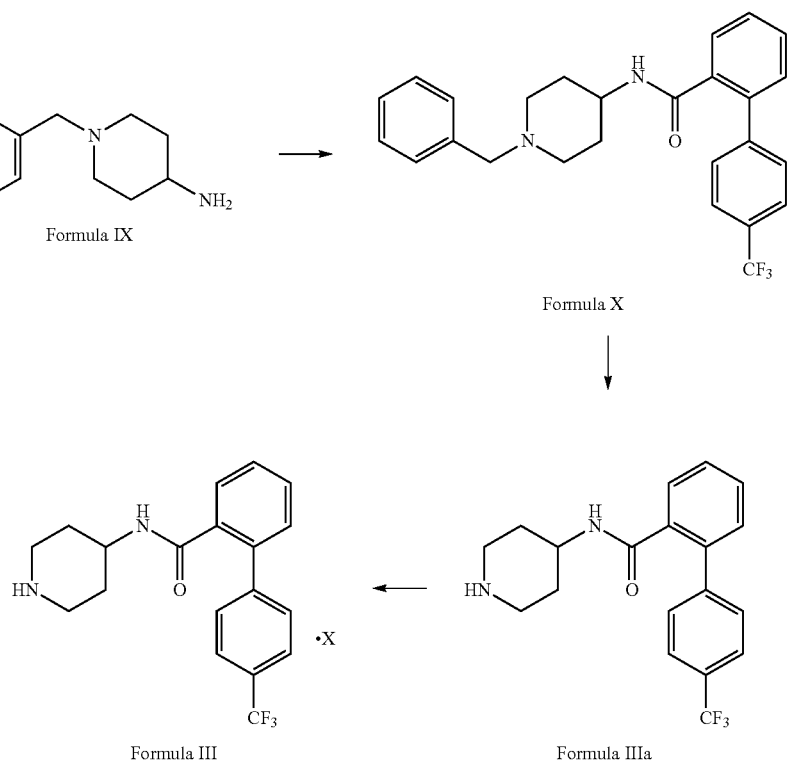

Formula X

Formula III        Formula IIIa wherein X represents an acid salt.

In another embodiment of the present invention, aliphatic alcohols are selected from the group comprising of methanol, ethanol, n-propanol, isopropanol, n-butanol, pentanol, isobutanol, tertiary butanol, cyclopropanol, cyclobutanol, cyclopentanol, cyclohexanol or mixtures thereof, aromatic alcohols are selected form the group comprising of phenols, benzylalcohol or mixtures thereof; chlorinated hydrocarbons are selected from the group comprising of chloroform, ethylene chloride, methylene dichloride or mixtures thereof; organic nitriles are selected from the group comprising of aliphatic nitriles such as $C_2$-$C_8$ nitrile; Ketones are selected from the group comprising of aliphatic ketones such as acetone, dimethyl formamide, methyl ethyl ketone, methyl isobutyl ketone, cyclobutanone, cyclopentanone, cyclohexanone or mixtures thereof; esters are selected from the group comprising of methyl acetate, ethyl acetate, isopropyl acetate, isopropyl acetate or mixtures thereof; non-polar solvents are selected from the group comprising of butane, pentane, hexane, heptane, toluene, n-hexane, n-heptane and hydroxide, lithium hydroxide and the like; metal alkoxides used throughout the invention are selected form the group comprising of sodium methoxide, sodium ethoxide, potassium methoxide, potassium ethoxide and the like.

In another embodiment of the present invention, acid salt used throughout the invention is selected from the group comprising of organic acid salts like acetate salt, formate salt, oxalate, methane sulfonate salt; inorganic acid salts like hydrochloride salt, hydrobromide salt and the like.

In another embodiment of the present invention, metal catalyst used throughout the invention is selected form the group comprising of palladium and platinum and the like.

In another embodiment of the present invention provides a compound, 9-(4-acetoxybutyl-9H-fluorene-9-carboxylic acid of Formula V useful in the process for the preparation of Lomitapide or its pharmaceutically acceptable salt thereof.

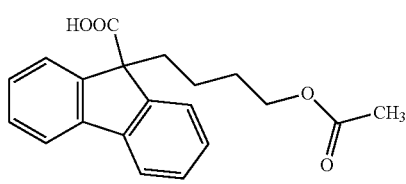

Formula V

In another embodiment of the present invention, obtained compound of formula V can be optionally isolated and purified by conventional methods.

In another embodiment of the present invention provides a compound, 9-(4-hydroxybutyl)-9H-fluorene-9-carboxylic acid of Formula VI useful in the process for the preparation of Lomitapide or its pharmaceutically acceptable salt thereof.

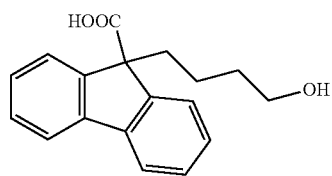

Formula VI

In another embodiment of the present invention, obtained compound of formula VI can be optionally isolated and purified by conventional methods.

The invention of the present application will be explained in more detail with reference to the following examples, which should not be construed as limiting the scope of the invention in any manner.

EXAMPLES

Preparation of 9-(4-Bromobutyl)-N-(2,2,2-trifluoroethyl-9H-fluorene-9-carboxamide of Formula II To a solution of 9-fluorenecarboxylic acid (50 g, 240 mmol) in THF (1200 mL) at 0° C., was added dropwise a solution of n-butyl lithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. HCl solution (1N, 500 mL) was added, then extracted with dichloromethane (3×750 mL) to give 9-(4-bromobutyl)-9H-fluorene-9-carboxylic acid (71 g, 85%) as a white solid.

To a solution of above obtained acid (60 g, 173 mmol) and DMF (100 µL) in CH$_2$Cl$_2$ (600 mL) under argon at 0° C. was added oxalyl chloride (104 mL, 2.0M in CH$_2$Cl$_2$, 208 mmol) drop wise. The reaction was stirred at 0° C. for 10 min, then warmed to RT and stirred for 1.5 h. The reaction was concentrated to give the crude acid chloride as yellow oil. To a suspension of 2,2,2-trifluoroethylamine hydrochloride (25.9 g, 191 mmol) in CH$_2$Cl$_2$ (500 mL) at 0° C. under argon was added triethylamine (73 mL, 521 mmol) followed by drop wise addition of a solution of the crude acid chloride in CH$_2$Cl$_2$ (15 mL). The reaction was stirred at 0° C. for 1 h, diluted with CH$_2$Cl$_2$ (500 mL), and washed with water (2×300 mL), 1N HCl (2×300 mL) to give 80 g of an oil which was purified by flash chromatography on silica gel (2.5 kg). The crude product was loaded in a mixture of CH$_2$C$_{12}$ and hexane, and eluted with a step gradient of 10% EtOAc/hexane (4 L) to 15% EtOAc/hexane (2 L) to 20% EtOAc/hexane (4 L). Pure fractions were combined and evaporated to give 9-(4-bromobutyl)-N-(2,2,2-trifluoroethyl-9H-fluorene-9-carboxamide of formula II as a white solid.
Yield: 52.5 gm.
Chromatographic purity (by HPLC):<90%.
Dimer impurity A: 12.11%.

Preparation of N-(1-Piperidin-4-yl)-4,-(trifluoromethyl)-[1,1'-biphenyl]-2-carboxamide Compound of Formula IIIa To a slurry of 4'-(trifluoromethyl)-2-biphenyl carboxylic acid of Formula VIII (50.0 g, 190 mmol) in methylene chloride (500 ml) was added the oxalyl chloride (28.7 ml, 330 mmol) followed by DMF (5 drops). The reaction mixture was stirred and the residue was dissolved in methylene chloride (400 ml). This solution was added drop wise to a solution of 4-amino-1-benzylpiperidine of Formula IX (36.4 ml, 180 mmol) and triethylamine (65.4 ml, 470 mmol) in methylene chloride (300 ml). The reaction was diluted with methylene chloride (600 ml) and washed with saturated NaHCO$_3$ and 1N KOH. The organic layer was dried with Na$_2$SO$_4$, and the solvent removed to give a white solid. This solid was recrystallized from hot EtOH (1 L) and washed with heptane to give N-(1-benzylpiperidin-4-yl)-4'-(trifluoromethyl)-[1,1'-biphenyl]-2-carboxamide compound of Formula X as a white solid (59.1 g, 75.6% yield). The mother liquor was concentrated to dryness and recrystallized from hot EtOH (300 ml) and washed with heptane to give N-(1-benzylpiperidin-4-yl)-4'-(trifluoromethyl)-[1,1'-biphenyl]-2-carboxamide compound of Formula X as a white solid.
Yield: 12.7 gm.

To a solution of benzoylpiperidinyl biphenyl carboxamide derivative of of Formula X (59.0 g, 130 mmol) in methanol (300 ml) and ethanol (300 ml) was added the cyclohexene (150 ml, 1.5 mol) and 20% palladium hydroxide on carbon (11.8 g). The reaction was heated to reflux (80° C.) and stirred at that temperature 2.5 h. The hot mixture was filtered and washed with methanol and then solvent was removed to give N-(1-piperidin-4-yl)-4,-(trifluoromethyl)-[1,1'-biphenyl]-2-carboxamide compound of Formula IIIa as a white solid.
Yield: 46.7 gm.
Chromatographic purity (by HPLC):≤91%.
Dimer impurity B: 6%.

Preparation of Lomitapide Free Base

To a stirred solution of N-(1-piperidin-4-yl)-4,-(trifluoromethyl)-[1,1'-biphenyl]-2-carboxamide compound of Formula IIIa (18.0 g, 49 mmol) in dimethyl formamide (100 ml) at room temperature was added potassium carbonate (12.6 g, 49 mmol) followed by 9-(4-bromobutyl)-N-(2,2,2-trifluoroethyl-9H-fluorene-9-carboxamide of formula II (21.0 g, 49 mmol). The reaction was heated to 50° C. and stirred at that temp under argon 24 h. After cooling, the reaction was filtered to remove potassium carbonate, and the filter cake was rinsed with ethyl acetate. The filtrate was partitioned between 20% heptane in ethyl acetate and water. The organic layer was dried (Na$_2$SO$_4$) and the solvent removed in vacuo to give a solid (30 g). This solid was recrystallized from 300 ml 25% ethyl acetate in heptane to give Lomitapide Free base as an off-white solid (27.0 g, 78.9% yield).
Yield: 27.0 gm.
Chromatographic purity (by HPLC):≤85%.

Example 1

Preparation of 9-(4-Acetoxybutyl)-9H-fluorene-9-carboxylic acid of Formula V Tetrahydrofuran (1700 ml) was added to the 9H-fluorene-9-carboxylic acid (100 gm) at room temperature then the reaction mass was cooled to −20 to −30° C. n-butyl lithium (67 gm) was added slowly at −20 to −30° C. for 60 to 90 minutes and maintained for 60 to 70 minutes at −20 to −30° C. 4-bromobutyl acetate (185 gm) was added then the reaction mass was cooled to room temperature and maintained for 17 hours. After completion of the reaction, DM water was added to the reaction mixture and stirred for 30 minutes at room temperature to yield 9-(4-acetoxybutyl)-9H-fluorene-9-carboxylic acid of Formula V.

Example 2

Preparation of 9-(4-Hydroxybutyl)-9H-fluorene-9-carboxylic acid of Formula VI To the above reaction mixture, 10% NaOH solution was added at room temperature. After completion of the reaction, reaction mass was washed with dichloromethane and pH was adjusted to 1 to 1.5 with 50% HCl solution. Filtered the solid and washed with DM water then dried at room temperature to yield crude 9-(4-hydroxybutyl)-9H-fluorene-9-carboxylic acid. Charged Dichloromethane to the above solid at room temperature and stirred for 5 to 6 hours at room temperature. Filtered the solid and washed with dichloromethane then dried the material to yield pure 9-(4-hydroxybutyl)-9H-fluorene-9-carboxylic acid of formula VI.
Yield: 107 gm.
Chromatographic purity (by HPLC): 96.6%.

Example 3

Preparation of 9-(4-Hydroxybutyl)-N-(2,2,2-trifluoroethyl)-9H-fluorene-9-carboxamide of Formula VII Charged dichloromethane (500 ml) to the above solid (100 gm) at room temperature and then cooled to 0 to 10° C. 2,2,2-trifluoroethan-1-amine HCl salt (57 gm) was added and followed by adding DM water and dichloromethane (200 ml), 10% NaOH solution was added at 0 to 10° C. and the layers ware separated. The aqueous layer was washed with dichloromethane (200 ml). Combined the layers and charged 3-(ethylimino methyleneamino)-N,N-dimethyl-propan-1-amine HCl (EDCl.HCl) (71 gm). Reaction mass was maintained for 1 hour to 1 hour 30 minutes at 0 to 10° C. and filtered the mass then washed with dichloromethane. Distilled off the solvent completely and added acetonitrile (300 ml) to the obtained product and added slowly DM water then stirred for 14 hours to 15 hours. Filtered the solid and washed with diisopropyl ether (300 ml) and dried to yield 9-(4-Hydroxybutyl)-N-(2,2,2-trifluoroethyl)-9H-fluorene-9-carboxamide of Formula VII.
Yield: 90 gm
Chromatographic purity (by HPLC): 97.3%.

Example 4

Preparation of 9-(4-Bromobutyl)-N-(2,2,2-trifluoroethyl)-9H-fluorene-9-carboxamide of Formula II To the above 9H-fluorene-9-carboxamide derivative of formula VII (100 gm), triphenylphosphine (144 gm) and dichloromethane (500 ml) were added at 25 to 30° C. then cooled to 0° C. to 10° C. Bromine solution (88 gm of bromine and 400 ml of dichloromethane) was added to the above reaction mixture then maintained for 15 to 30 minutes at 0° C. to 10° C. Reaction mixture was heated to 25 to 30° C. After the completion of reaction, sodium thiosulphate solution was added and stirred for 10 minutes then layers were separated. Organic layer was washed with 10% NaOH solution and DM water then distilled the layer followed by drying, diisopropyl ether (800 ml) was added and stirred for hours at 20 to 30° C. Filtered the solid and washed with diisopropyl ether (600 ml). Distilled the solid and filtered the reaction mixture and washed with dichloromethane (1000 ml). Filtered the solid and washed with hexane then dried to yield 9-(4-bromobutyl)-N-(2,2,2-trifluoroethyl)-9H-fluorene-9-carboxamide of Formula II.
Yield: 85 gm.
Chromatographic purity (by HPLC): 98.6%.

Example 5

Preparation of N-(1-Benzylpiperidin-4-yl)-4'-(trifluoromethyl)-[1,1'-biphenyl]-2-carboxamide of Formula X Charged 4'-(trifluoromethyl)-[1,1'-biphenyl]-2-carboxylic acid of Formula VIII (100 gm) and acetonitrile (1000 ml) at 25 to 30° C. and then stirred for 5 minutes to 10 minutes. Charged 4-amino-1-benzylpiperidine of Formula IX (70 gm) to the above reaction mixture and stirred for 5 minutes to 10 minutes at 25 to 30° C. Hydroxybenzotriazole (HOBT) (7 gm) was added and stirred for 5 minutes to 10 minutes at 25 to 30° C. To the above reaction mixture, EDC.HCl (80 gm) and acetonitrile (500 ml) were added at 25 to 30° C. and then stirred for 3 hours to 3 hours 30 minutes. Filtered the solid and washed with acetonitrile (300 ml) and then dried the material at 35 to 40° C. for 5 to 6 hours to yield N-(1-benzylpiperidin-4-yl)-4'-(trifluoromethyl)-[1,1'-biphenyl]-2-carboxamide of Formula X.
Yield: 140 gm
Chromatographic purity (by HPLC): 99%.

Example 6

Preparation of Hydrochloride salt of N-(1-Piperidin-4-yl)-4'-(trifluoromethyl)-[1,1'-biphenyl]-2-carboxamide of Formula III To the benzylpiperidinyl biphenyl carboxamide derivative of Formula X (100 gm) compound, added methanol (1200 ml) and 10% Pd/C in DM water. Reaction mixture was heated to 45 to 55° C. and maintained for 3 hours to 3 hours 30 minutes. The reaction mixture was cooled to 25 to 30° C. and filtered the material and washed with methanol (400 ml). Methanol was distilled-off completely at 45 to 50° C. Methanol (200 ml) was added at 25 to 30° C. and stirred for 5 minutes at room temperature. Conc.Hydrochloric acid (200 ml) was added and stirred for 15 minutes to 20 minutes at 30 to 35° C. DM water was added and maintained for 1 hour to 1 hour 30 minutes at 30 to 35° C. and filtered the solid then washed with water. Dried the material to yield hydrochloride salt of N-(1-Piperidin-4-yl)-4'-(trifluoromethyl)-[1,1'-biphenyl]-2-carboxamide of Formula III.
Yield: 60 gm
Chromatographic purity (by HPLC): 97.8%.

Example 7

Preparation of Lomitapide Free Base

Charged N-(1-piperidin-4-yl)-4'-(trifluoromethyl)-[1,1'-biphenyl]-2-carboxamide hydrochloride salt of Formula III (100 gm) and dimethyl formamide (300 ml) to the 9-(4-bromobutyl)-N-(2,2,2-trifluoroethyl)-9H-fluorene-9-carboxamide of Formula II (121 gm) at 25 to 30° C. and stirred for 15 to 20 minutes. Triethylamine (78 gm) was added to the above reaction mixture for 30 minutes to 45 minutes at room temperature. The reaction mixture was maintained for 21 hours to 23 hours at 25 to 30° C. Filtered the sold and washed with dimethyl formamide (100 ml) and the layers were separated. DM Water was added to the organic layer and then combined the layers at 25 to 30° C. Maintained the reaction mixture for 6 hours to 7 hours at room temperature and filtered the solid and washed with water. Acetonitrile was added and heated to 75 to 80° C. The obtained clear solution was cooled to room temperature and stirred for 90 hour 120 minutes at 25 to 30° C. Filtered the solid and washed with acetonitrile and dried the compound to yield Lomitapide Free base.

Yield: 60 gm.
Chromatographic purity (by HPLC): 99.8%.

Example 8

Preparation of Lomitapide Mesylate

Charged methanol (250 ml) at to Lomitapide free base (50 gm) at 25 to 30° C. and cooled to 0 to −10° C. Methane sulfonic acid (6 gm) was added at 0 to −10° C. for 30 minutes to 45 minutes. Maintained the above obtained reaction mixture at 0 to −10° C. for 45 minutes to 60 minutes. Activated carbon was added at 0 to −10° C. and maintained for 30 minutes to 60 minutes. Filtered the material and washed with methanol (200 ml) and methanol was distilled off completely at 35 to 40° C. and followed by drying to yield Lomitapide Mesylate.

Yield: 55 gm.
Chromatographic purity (by HPLC): 99.4%.

We claim:

1. A process for the preparation of Lomitapide or its pharmaceutically acceptable salt thereof of Formula I, Formula I wherein X represents an acid salt,
the method comprising,
i) condensing a 9H-fluorene-9-carboxylic acid of Formula IV Formula IV with 4-bromobutyl acetate to yield 9-(4-acetoxybutyl)-9H-fluorene-9-carboxylic acid of Formula V;

Formula V ii) optionally isolating the compound of Formula V;
iii) reacting the compound of Formula V with an alkali hydroxide solution to yield 9-(4-hydroxybutyl)-9H-fluorene-9-carboxylic acid of Formula VI;

Formula VI iv) reacting the compound of Formula VI with 2,2,2-trifluoroethane-1-amine hydrochloride salt to yield 9-(4-hydroxybutyl)-N-(2,2,2-trifluoroethyl)-9H-fluorene-carboxylic acid of Formula VII;

Formula VII v) reacting the compound of Formula VII with bromine to yield a bromobutyl 9H-fluorene carboxamide compound of Formula II;

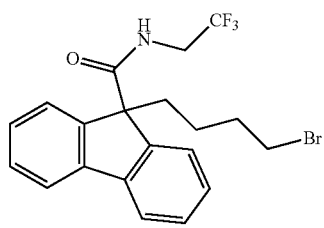

Formula II vi) optionally purifying the compound of Formula II;
vii) condensing the compound of Formula II with a salt of piperidinyl biphenyl carboxamide compound of Formula III

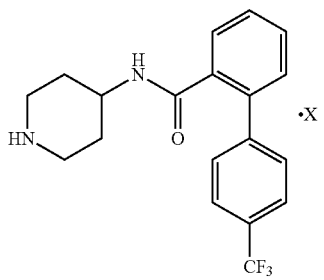

Formula III wherein X represents an acid salt to yield Lomitapide freebase;
viii) optionally purifying Lomitapide free base;
ix) optionally converting Lomitapide free base to its pharmaceutically acceptable salt of Formula I; and
x) optionally purifying the Lomitapide pharmaceutically acceptable salt of Formula I.

2. The process as claimed in claim 1, further comprising a solvent in step i), wherein the solvent used in step i) is selected from the group consisting of alcohols, halogenated hydrocarbons, polar aprotic solvents, and non-polar solvents, wherein alcohols are selected from the group consisting of aliphatic alcohols, and aromatic alcohols; halogenated hydrocarbons are selected from the group consisting of chlorinated hydrocarbons; and polar aprotic solvents are selected from the group consisting of organic nitriles, amides, ketones, ethereal solvents, esters and mixtures thereof.

3. The process as claimed in claim 1, further comprising a base in step i), wherein the base used in step i) is selected from the group consisting of triethyl amine, n-butyl lithium, sec-butyl lithium, sodium hydride, potassium hydride, sodium hydroxide, and potassium hydroxide.

4. The process as claimed in claim 1, wherein the alkali hydroxide used in step iii) is selected from the group consisting of sodium hydroxide, potassium hydroxide, and lithium hydroxide.

5. The process as claimed in claim 1, further comprising a solvent in step vii), wherein the solvent used in step vii) is selected from the group consisting of methanol, ethanol, methylene chloride, acetonitrile, acetone, ethyl acetate, dimethyl formamide, and mixtures thereof.

6. The process as claimed in claim 1, further comprising a solvent in step viii), wherein the solvent used in step viii) is selected from the group consisting of methanol, ethanol, methylene chloride, acetonitrile, acetone, ethyl acetate, n-heptane, n-hexane, toluene, dimethyl formamide, and mixtures thereof.

7. The process as claimed in claim 1, wherein the acid X used in step ix) is selected from the group consisting of methane sulfonic acid, acetic acid, formic acid, oxalic acid, hydrochloric acid, and hydro-bromic acid.

8. The process as claimed in claim 1, further comprising a solvent in step ix), wherein the solvent used in step ix) is selected from the group consisting of methanol, ethanol, isopropyl alcohol, methylene chloride, acetonitrile, acetone, ethyl acetate, n-heptane, n-hexane, toluene, and mixtures thereof.

9. The process as claimed in claim 1, further comprising a solvent in step x), wherein the solvent used in step x) is selected from the group consisting of methanol, ethanol, isopropyl alcohol, methylene chloride, acetonitrile, acetone, ethyl acetate, n-heptane, n-hexane, toluene, and mixtures thereof.

10. The process according to claim 1, wherein the preparation of the salt of piperidinyl biphenyl carboxamide compound of Formula III,
comprises:
a) condensing 4'-(trifluoromethyl)-[1,1'-biphenyl]-2-carboxylic acid of Formula VIII

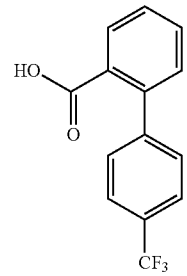

Formula VIII with 4-amino-1-benzyl piperidine of Formula IX

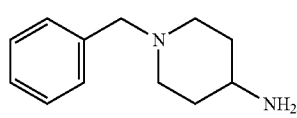

Formula IX to yield benzylpiperidine biphenyl carboxamide compound of Formula X;

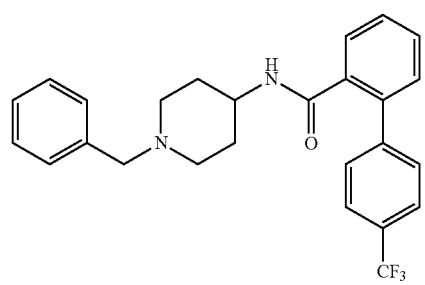

Formula X b) optionally isolating the compound of Formula X;
c) optionally purifying the compound of Formula X; and
d) converting the compound of Formula X to an acid salt of piperidinyl biphenyl carboxamide compound of Formula III.

11. The process as claimed in claim 10, further comprising a solvent to form the compound of Formula X in step a), wherein the solvent used in step a) is selected from the group consisting of methanol, ethanol, isopropanol, methylene chloride, dimethyl formamide, ethyl acetate, isopropyl acetate, acetonitrile, heptane, toluene, n-heptane, n-hexane, diisopropyl ether, tetrahydrofuran, 1,4-dioxane, and mixtures thereof.

12. The process as claimed in claim 10, wherein the converting of the compound of Formula X to the acid salt of piperidinyl biphenyl carboxamide of Formula III in step d) comprises a debenzylation, wherein the debenzylation is carried out using a metal catalyst selected from the group consisting of palladium and platinum.

13. The process as claimed in claim 10, wherein the converting of the compound of Formula X to the acid salt of piperidinyl biphenyl carboxamide of Formula III in step d) of claim 10 comprises the use of an acid, wherein the acid is selected from the group consisting of hydrochloric acid, hydrobromic acid, acetic acid and formic acid.

* * * * *